(12) United States Patent
Santucci-Aribert et al.

(10) Patent No.: US 10,066,182 B2
(45) Date of Patent: Sep. 4, 2018

(54) LUBRICANT COATING FOR MEDICAL CONTAINER

(71) Applicant: Becton Dickinson France, Le Pont de Claix (FR)

(72) Inventors: Virginie Santucci-Aribert, Moirans (FR); Emanuela Rossito, Saint-Egreve (FR)

(73) Assignee: Becton Dickinson France, Le Pont de Claix (FR)

( * ) Notice: Subject to any disclaimer, the term of this patent is extended or adjusted under 35 U.S.C. 154(b) by 320 days.

(21) Appl. No.: 14/399,192

(22) PCT Filed: May 7, 2013

(86) PCT No.: PCT/EP2013/059531
§ 371 (c)(1),
(2) Date: Nov. 6, 2014

(87) PCT Pub. No.: WO2013/167617
PCT Pub. Date: Nov. 14, 2013

(65) Prior Publication Data
US 2015/0322366 A1    Nov. 12, 2015

(30) Foreign Application Priority Data

May 7, 2012   (EP) .................................... 12305508

(51) Int. Cl.
*C10M 107/50*   (2006.01)
*B05D 5/08*   (2006.01)
(Continued)

(52) U.S. Cl.
CPC ........... *C10M 107/50* (2013.01); *A61L 29/06* (2013.01); *A61L 29/14* (2013.01); *A61M 5/3129* (2013.01);
(Continued)

(58) Field of Classification Search
CPC ... C08L 83/00; C09D 183/04; A61L 2400/10; A61L 29/06; A61L 29/14;
(Continued)

(56) References Cited

U.S. PATENT DOCUMENTS

| 4,181,223 A | 1/1980 | Millet |
| 4,496,695 A | 1/1985 | Sugio et al. |

(Continued)

FOREIGN PATENT DOCUMENTS

| EP | 0227340 A2 | 7/1987 |
| EP | 0743072 A2 | 11/1996 |

(Continued)

*Primary Examiner* — Yan Lan
(74) *Attorney, Agent, or Firm* — The Webb Law Firm (57) ABSTRACT

The invention relates to a lubricant coating for a medical container comprising a cross-linked lubricant composition comprising a mixture of non-reactive silicone with reactive silicone, characterized in that the reactive silicone comprises a mixture of vinyl-based silicone and acrylate-based silicone. The invention further relates to a lubricant composition usable as an intermediate product in the fabrication of a lubricant coating. The invention further relates to a medical container comprising a barrel and a stopper in gliding engagement within the barrel, comprising such a lubricant coating. The invention also relates to a process of manufacturing a medical container comprising a barrel and a stopper in gliding engagement within the barrel including depositing a lubricant composition on the inner surface of the barrel and/or on the stopper, and irradiating the coated barrel and/or stopper so as to cross-link the lubricant composition to form a lubricant coating.

12 Claims, 3 Drawing Sheets

(51) Int. Cl.
| | |
|---|---|
| *B65D 39/00* | (2006.01) |
| *B05D 3/06* | (2006.01) |
| *A61M 5/31* | (2006.01) |
| *A61L 29/06* | (2006.01) |
| *A61L 29/14* | (2006.01) |
| *C09D 183/04* | (2006.01) |
| *C08G 77/20* | (2006.01) |

(52) U.S. Cl.
CPC .............. *B05D 3/068* (2013.01); *B05D 5/08* (2013.01); *B65D 39/0005* (2013.01); *C09D 183/04* (2013.01); *A61L 2400/10* (2013.01); *A61M 2005/3131* (2013.01); *B65D 2539/008* (2013.01); *C08G 77/20* (2013.01); *C10M 2229/0415* (2013.01); *C10M 2229/0435* (2013.01); *C10N 2220/022* (2013.01); *C10N 2230/06* (2013.01); *C10N 2230/10* (2013.01); *C10N 2230/68* (2013.01); *C10N 2240/66* (2013.01); *C10N 2250/10* (2013.01); *C10N 2250/121* (2013.01)

(58) Field of Classification Search
CPC ........ A61M 2005/3131; A61M 5/3129; B65D 2539/008; B65D 39/0005; C10M 107/50; C10M 2229/0415; C10M 2229/0435; C10N 2220/022; C10N 2230/06; C10N 2230/10; C10N 2230/68; C10N 2240/66; C10N 2250/10; C10N 2250/121
See application file for complete search history.

(56) References Cited

U.S. PATENT DOCUMENTS

| | | |
|---|---|---|
| 4,500,310 A | 2/1985 | Christinger |
| 4,640,939 A | 2/1987 | Cavezzan et al. |
| 4,764,576 A | 8/1988 | Ogawa et al. |
| 4,806,430 A | 2/1989 | Spielvogel et al. |
| 5,064,083 A | 11/1991 | Alexander et al. |
| 5,338,312 A | 8/1994 | Montgomery |
| 5,536,582 A | 7/1996 | Prasad et al. |
| 5,587,244 A | 12/1996 | Flinchbaugh |
| 5,662,960 A | 9/1997 | Hostettler et al. |
| 5,736,251 A | 4/1998 | Pinchuk |
| 5,911,711 A | 6/1999 | Pelkey |
| 6,015,398 A | 1/2000 | Arimatsu et al. |
| 6,200,627 B1 | 3/2001 | Lubrecht |
| 6,296,893 B2 | 10/2001 | Heinz et al. |
| 6,406,792 B1 | 6/2002 | Briquet et al. |
| 6,461,334 B1 | 10/2002 | Buch-Rasmussen et al. |
| 6,482,509 B2 | 11/2002 | Buch-Rasmussen et al. |
| 6,586,039 B2 | 7/2003 | Heinz et al. |
| 7,141,042 B2 | 11/2006 | Lubrecht |
| 8,075,995 B2 | 12/2011 | Zhao et al. |
| 2001/0004466 A1 | 6/2001 | Heinz et al. |
| 2004/0209784 A1 | 10/2004 | Hardman et al. |
| 2011/0276005 A1 | 11/2011 | Hioki et al. |
| 2012/0053530 A1 | 3/2012 | Zhao et al. |
| 2012/0058351 A1 | 3/2012 | Zhao et al. |

FOREIGN PATENT DOCUMENTS

| | | |
|---|---|---|
| EP | 0920879 A2 | 6/1999 |
| EP | 0962229 A2 | 12/1999 |
| EP | 0972811 A1 | 1/2000 |
| EP | 1004612 A1 | 5/2000 |
| EP | 1060031 A1 | 12/2000 |
| EP | 1083205 A1 | 3/2001 |
| EP | 1341860 A1 | 9/2003 |
| EP | 2226088 A1 | 9/2010 |
| JP | 6197965 A | 7/1994 |
| JP | 2003180832 A | 7/2003 |
| JP | 2004321614 A | 11/2004 |
| JP | 2007244606 A | 9/2007 |
| JP | 2010201844 A | 9/2010 |
| WO | 2004009146 A1 | 1/2004 |
| WO | 2004064901 A2 | 8/2004 |
| WO | 2004083348 A2 | 9/2004 |
| WO | 2007115156 A2 | 10/2007 |
| WO | 2008034060 A2 | 3/2008 |

LUBRICANT COATING FOR MEDICAL CONTAINER

CROSS-REFERENCE TO RELATED APPLICATIONS

This application is the United States national phase of International Application No. PCT/EP2013/059531 filed May 7, 2013, and claims priority to European Patent Application No. 12305508.9 filed May 7, 2012, the disclosures of which are hereby incorporated in their entirety by reference.

FIELD OF THE INVENTION

The invention relates to a lubricant coating and a lubricant composition for a medical container and a medical container comprising such a coating.

TECHNICAL BACKGROUND

Medical containers comprising a stopper in gliding engagement within a barrel are widely used to deliver drug to patients.

Such containers include syringes, cartridges and auto-injectors.

They are preferably prefilled in order to be more easily used by a patient or by medical staff, and to eliminate the risk of contamination that occurs when a drug is transferred from a vial to an injection device.

Such medical containers are usually lubricated to ensure a good gliding movement of the stopper within the barrel when the drug is injected to a patient.

The gliding movement of the stopper involves the application of an activation force to put the stopper in motion, then of a gliding force to maintain the motion of the stopper.

In order to have a smooth gliding and to avoid any stick-slip effect, the activation force and gliding force have to be as low as possible.

Lubricant may consist in mineral or vegetable oil or in a synthetic lubricant.

Silicone oil such as poly-(dimethylsiloxane) is widely used as lubricant for such applications.

However, such silicone oil has the drawback of being unstable over time and especially after autoclave treatments that are usually performed to ensure the sterility of the medical container, before or after the filling of the medical containers with pharmaceutical compositions.

Due to ageing or to such treatments, it is common to observe squeeze-out of the lubricant under the pressure exerted between the stopper and the barrel.

However, if the lubricant squeezes-out i.e. migrates from the interface between the stopper and the barrel, the activation force of the stopper becomes higher and does not allow for a smooth gliding of the stopper.

The accuracy of the delivered dose of a pharmaceutical solution contained into the medical container is therefore decreased particularly when the injection is performed by a pump.

Document EP 0 920 879 proposes a lubricant composition consisting of a mixture of non-reactive silicone oil and reactive silicone, namely a vinyl-based silicone, with a fraction of non-reactive silicone in the mixture comprised between 5 and 85% by weight.

The composition is then applied to a medical container and subjected to a cross-linking treatment.

As a result, the coating forms a solid film along the inner wall of the barrel.

However, such a coating still presents poor mechanical performances, i.e. high activation and gliding forces.

In particular, the activation force remains higher than the maximum desired limit.

BRIEF DESCRIPTION OF THE INVENTION

A goal of the invention is to provide a lubricant coating for medical containers that does not present the drawbacks of the known coatings.

More precisely, this lubricant coating should provide better gliding properties, have a good stability to sterilization treatments and a good stability over time (including a storage time comprised between 12 to 24 months).

In addition, the lubricant coating should not interact with the pharmaceutical composition that is intended to be filled into the medical container.

In particular, the lubricant coating should not contain elements that could be extracted to the pharmaceutical composition stored in the container.

A goal of the invention is to provide a lubricant composition that can be used as an intermediate product in the fabrication of such a lubricant coating.

According to an embodiment, the invention provides a lubricant coating for a medical container comprising a cross-linked lubricant composition comprising a mixture of non-reactive silicone with reactive silicone, wherein the reactive silicone comprises a mixture of vinyl-based silicone and acrylate-based silicone.

"Reactive silicone" means a silicone polymer comprising at least one reactive functional group, i.e. a functional group that polymerizes under usual conditions of irradiation (e.g. Gamma or UV irradiation). A reactive functional group thus usually comprises at least one chemical bond that is able to break under irradiation and to link up with another functional group for creating a polymer.

"Non-reactive" silicone means a silicone polymer that only comprises non-reactive functional groups, i.e. functional groups that do not polymerize under usual conditions of irradiation, and that does not comprise any reactive functional group as defined above. For example, linear alkyl chains are considered to be non-reactive functional groups within the meaning of the present invention.

Advantageously, said lubricant coating comprises a three-dimensional solid structure formed of cross-linked reactive functional groups of the reactive silicone and a liquid phase comprising non-reactive silicone, said liquid phase being retained within said three-dimensional solid structure.

Non-cross-linked coatings, i.e. coatings that do not present a cross-linked solid network enclosing a liquid phase are outside of the scope of the invention.

According to a preferred embodiment, the amount of the non-reactive silicone is comprised between 80 and 90% by weight relative to the total weight of the lubricant composition.

According to a preferred embodiment, the amount of vinyl-based silicone in the lubricant composition is comprised between 8 and 15% by weight and the amount of the acrylate-based silicone in the lubricant composition is comprised between 2 and 5% by weight.

According to a preferred embodiment, the amount of vinyl-based silicone in the lubricant composition is 10% by weight and the amount of the acrylate-based silicone in the lubricant composition is 3% by weight.

The non-reactive silicone may be poly-(dimethylsiloxane).

The vinyl-based silicone may comprise a trimethylsilyl terminated vinylmethylsiloxane-dimethylsiloxane copolymer.

The acrylate-based silicone may comprise a trimethylsilyl terminated acryloxypropylmethylsiloxane-dimethylsiloxane copolymer.

Preferably, said lubricant coating has a gel structure with a gel fraction comprised between 25 and 55% by weight.

Advantageously, said lubricant coating has a shear viscosity comprised between 500 and 2000 Pa·s for a shear rate of 0.1 rad/s at 25° C.

Advantageously, said lubricant coating has a phase angle comprised between 20° and 40° for a shear rate of 0.1 rad/s at 25° C.

According to an embodiment, the invention provides a lubricant composition that can be used as an intermediate product in the fabrication of a lubricant coating for a medical container.

Said lubricant composition comprises a mixture of non-reactive silicone with reactive silicone, wherein the reactive silicone comprises a mixture of vinyl-based silicone and acrylate-based silicone.

According to a preferred embodiment, the amount of the non-reactive silicone is comprised between 80 and 90% by weight relative to the total weight of the lubricant composition.

According to a preferred embodiment, the amount of vinyl-based silicone in the lubricant composition is comprised between 8 and 15% by weight and the amount of the acrylate-based silicone in the lubricant composition is comprised between 2 and 5% by weight.

According to a preferred embodiment, the amount of vinyl-based silicone in the lubricant composition is 10% by weight and the amount of the acrylate-based silicone in the lubricant composition is 3% by weight.

The non-reactive silicone may be poly-(dimethylsiloxane).

In a preferred embodiment, the viscosity of the poly-(dimethylsiloxane) is 12500 cSt at 25° C.

The vinyl-based silicone may comprise a trimethylsilyl terminated vinylmethylsiloxane-dimethylsiloxane copolymer.

The acrylate-based silicone may comprise a trimethylsilyl terminated acryloxypropylmethylsiloxane-dimethylsiloxane copolymer.

According to an embodiment, the invention provides a medical container comprising a barrel and a stopper in gliding engagement within the barrel, wherein at least one of the barrel and the stopper is at least partially coated with a lubricant coating as described above.

Preferably, the thickness of the coating is of at least 350 nm.

According to an embodiment, the coating covers up to 90% of the inner surface of the barrel.

The barrel is advantageously made of plastic.

According to an embodiment, the invention provides a process for manufacturing a medical container comprising a barrel and a stopper in gliding engagement within the barrel, comprising the steps of:
  depositing a lubricant composition on the inner surface of the barrel and/or on the stopper, wherein the lubricant composition comprises a mixture of non-reactive silicone with reactive silicone, the reactive silicone comprising a mixture of vinyl-based silicone and acrylate-based silicone, and
  carrying out an irradiation of the coated barrel and/or stopper so as to cross-link the lubricant composition to form a lubricant coating.

According to a preferred embodiment, said irradiation comprises Gamma irradiation, preferably produced by a Cobalt-60 source.

According to an embodiment, the invention provides the use of a mixture of vinyl-based silicone and acrylate-based silicone as a reactive silicone component in a lubricant composition comprising a mixture of non-reactive silicone and reactive silicone to form a lubricant coating by cross-linking said lubricant composition, for reducing the activation force of a stopper in gliding engagement within a barrel of a medical container, at least one of the inner surface of the barrel and/or the stopper being coated with said lubricant coating.

Preferably, the amount of vinyl-based silicone in the lubricant composition is comprised between 8 and 15% by weight and the amount of the acrylate-based silicone in the lubricant composition is comprised between 2 and 5% by weight.

In an advantageous embodiment, the medical container is subjected to at least one autoclave treatment after the formation of the lubricant coating.

According to an embodiment, the invention provides a method of reducing the activation and gliding forces of a stopper in gliding engagement with a barrel of a medical container, comprising the steps of:
  coating at least one of the barrel and the stopper with a lubricant composition comprising a mixture of non-reactive silicone and reactive silicone, the reactive silicone comprising a mixture of vinyl-based silicone and acrylate-based silicone, and
  cross-linking the lubricant composition to form a coating.

According to a preferred embodiment of said method, the vinyl-based silicone is between 8 and 15 weight % and the acrylate-based silicone is between 2 and 5 weight percent relative to the total weight of the lubricant composition.

In addition, said method may further comprise subjecting the medical container to at least one autoclave treatment after the step of forming a coating.

BRIEF DESCRIPTION OF THE DRAWINGS

Other features, embodiments and advantages of the invention will be apparent from the detailed description that follows, based on the appended drawings wherein.

DETAILED DESCRIPTION OF THE INVENTION

According to an embodiment of the invention, a composition for a lubricant coating of a medical container comprises a mixture of non-reactive silicone and reactive silicone.

The coated medical container can be for example a syringe. But the medical container can also be a cartridge, an auto-injector or any other injection devices comprising a stopper in sliding engagement within a barrel.

Figure 1:
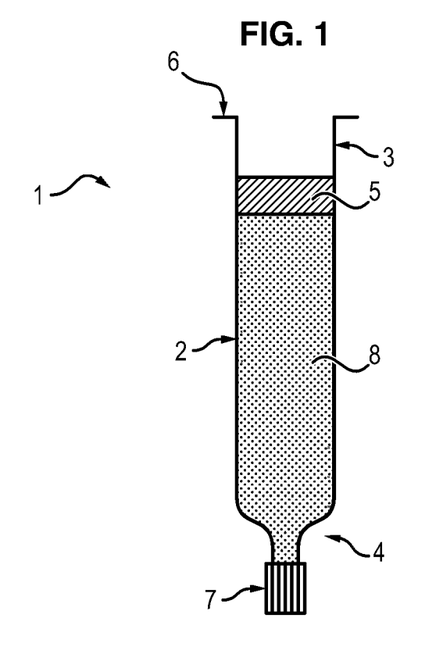
FIG. 1 shows a schematic view of a syringe.

As disclosed on FIG. 1, the syringe 1 comprises a barrel 2 with a flange 6, the syringe being closed at its proximal end 3 by a stopper 5 and at this distal end 4 by a cap 7.

The syringe 1 is filled with a pharmaceutical composition 8.

"Distal" means the part of the injection device the furthest from the hand of the user and the closest from the skin of the patient, "distally" meaning in the direction of the injection i.e. towards the patient.

"Proximal" means the part of the injection device the closest from the hand of the user and the furthest from the skin of the patient, "proximally" meaning in the direction opposite to the injection i.e. towards the user.

For example, the non-reactive silicone of the coating may comprise poly-(dimethylsiloxane) (PDMS), whose formula is:

with x between 70 and 1600.

According to a preferred embodiment, the amount of the non-reactive silicone within the lubricant composition is in the range from 80 to 90% by weight, preferably from 85 to 90% by weight and more preferably 87% by weight.

Preferably, the viscosity of the non-reactive silicone is comprised between 10 000 and 20 000 cSt at 25° C., when x is comprised between 845 and 970.

According to a preferred embodiment of the invention, the viscosity of the non-reactive silicone is comprised between 10 000 and 15 000 cSt.

More preferably, the non-reactive silicone consists of PDMS 12 500 cSt at 25° C.

For example, this non-reactive silicone is commercially available as PDMS-DC 360 from Dow Corning, Midland, USA.

In addition, the composition comprises reactive silicone, which comprises itself a mixture of vinyl-based silicone and acrylate-based silicone.

According to an advantageous embodiment, the vinyl-based silicone is a copolymer of vinylmethylsiloxane and dimethylsiloxane, with trimethylsilyl terminations, more precisely a block copolymer of vinylmethylsiloxane and dimethylsiloxane.

The formula of such a copolymer is for example:

with m comprised between 280 and 430, preferably 350 and n comprised between 18 and 28, preferably 23.

The viscosity of this vinyl-based silicone is comprised between 800 and 1200 cSt when measured at 25° C.

The amount of vinylmethylsiloxane within the copolymer is preferably between 7 and 8% in moles.

For example, this copolymer is commercially available from Gelest Inc, Morisville, USA under the name VDT-731, but other kind of vinylmethylsiloxane and dimethylsiloxane copolymers can be used, as alternative, periodic or statistical vinylmethylsiloxane and dimethylsiloxane copolymers.

By contrast, non-copolymer vinyl-based silicone does not provide as good results as above-mentioned copolymers.

According to an advantageous embodiment, the acrylate-based silicone is a copolymer of acryloxypropylmethylsiloxane and dimethylsiloxane with trimethylsilyl terminations.

The formula of such a copolymer is for example:

with p comprised between 60 and 80, preferably 76 and q comprised between 7 and 9, preferably 8.

The viscosity of this acrylate-based silicone is comprised between 80 and 120 cSt when measured at 25° C.

The amount of acryloxypropylmethylsiloxane within the copolymer is preferably comprised between 15 and 20% in moles.

For example, this copolymer is commercially available from Gelest Inc, Morisville, USA under the name UMS-182, but other kind of acrylatemethylsiloxane and dimethylsiloxane copolymers can be used, such as alternative, periodic or statistical acrylatemethylsiloxane and dimethylsiloxane copolymers.

According to a preferred embodiment, the amount of the reactive silicone within the lubricant composition is in the range from 10 to 20% by weight and more preferably between 10 to 15% by weight.

More precisely, the weight amount of the vinyl-based silicone is comprised from 8 to 15%, preferably from 8 to 12% and the weight amount of the acrylate-based silicone is ranging from 2 to 5%, preferably from 2 to 3% by weight of the lubricant composition.

According to a preferred embodiment of the present invention, the composition of the coating comprises 87% of non-reactive PDMS, 10% of vinyl-based silicone and 3% of acrylate-based silicone.

Additionally, further additives can be added in the lubricant composition, such as anti-oxidants, for example oxygen scavengers, UV filters, super-absorbent agents, polymers, excipients, fibers, mineral or metallic additives or any reinforcement materials.

For preparing the lubricant composition, the three above described components are mixed together.

If necessary, the obtained mixture is maintained for degassing after mixing, in order to remove air bubbles that may have formed during mixing.

Such a lubricant composition is in the form of a viscous fluid that can be applied onto the inner wall of a barrel of a medical container.

The application is usually performed at room temperature, but viscous compositions can be applied after being submitted to heat treatment.

In an alternative embodiment, the lubricant composition can be applied either after the barrel has been submitted to a heat treatment or directly after the molding or forming of the medical container, in order to allow a stronger adherence of this composition on the surface of the barrel.

The lubricant composition may also be applied onto a stopper before inserting it within the barrel.

In such case, the lubricant composition is applied onto at least the part of the surface of the stopper that is intended to be in contact with the barrel, but other parts of the surface of the stopper may also be covered by the lubricant composition.

The application of the lubricant composition is performed with tools that are known per se, for example spraying devices, which will thus not be described here in detail.

In order to provide desirable gliding properties, the thickness of the lubricant needs to be monitored.

Indeed, the thickness of the layer needs to be at least 350 nm, when measured by a reflectometry method.

Further, the lubricant composition is applied so as to cover up to 90% of the barrel.

In particular, if the medical container is a syringe, it may be preferred to apply the lubricant composition only in the center portion of the barrel, excluding both ends of the barrel.

For example, if the proximal end 3 of the barrel, located on the side of the plunger rod that actuates the stopper 5, is not lubricated, the removal of the stopper may be prevented, even if the stopper is itself lubricated. Indeed, the friction force would be very high on this non-lubricated part of the barrel, and an important force would be required in order to remove the stopper out of the barrel.

On the other hand, if the distal end 4 of the barrel, on the side of the injection port, is lubricated only on a portion of the barrel length, the stopper 5 remains capable of moving towards the injection port as a part of the lubricant coating is driven by the stopper. However, it may not be possible to move the stopper back due to consumption of the lubricant layer.

After application of the lubricant composition to the barrel and/or the stopper of a medical container, a cross-linking treatment can be carried out in order to cross-link the lubricant composition so as to form the lubricant coating.

Preferably, the lubricant coating consists of said cross-linked lubricant composition.

Said treatment may comprise Gamma-rays irradiation.

According to a preferred embodiment, the Gamma-rays irradiation is provided by a Cobalt-60 source with a dose ranging from 16 to 32 kGy.

Alternatively, other kind of cross-linking treatment may be carried out, for example UV or X-Ray irradiation or plasma polymerization.

The irradiation leads to the cross-linking of the coating composition, mainly by reaction between the reactive functional groups of the vinyl-based silicone and acrylate-based silicone and it has been shown that after irradiation the coating has a gel structure, i.e. a solid phase enclosing a liquid phase.

The composition of the coating therefore consists in a solid tridimensional molecular network of cross-linked vinyl-based and acrylate-based silicone that retains the liquid phase (corresponding to the free, non-cross-linked silicone).

It has been shown that this unique gel structure is only present when the reactive silicone comprises both vinyl-based and acrylate-based silicone.

Contrary to a plasma treatment that would cross-link only the superficial layer of the composition, Gamma or UV irradiation provides a substantially homogeneous gel structure on the whole thickness of the coating.

It can be noted that the thickness of the layer does not change after irradiation.

The gel structure may be defined by the following features:
- a gel fraction ranging between 25 and 55% by weight, determined by solvent swelling method (see below), and/or
- a shear viscosity ranging from 500 to 2000 Pa·s for a shear rate of 0.1 rad/s and at 25° C., and/or
- a phase angle comprised between 20 and 40° for a shear rate of 0.1 rad/s and at 25° C.

The shear viscosity and the phase angle, which characterize the visco-elastic behavior of the polymer, are measured with a rheometer.

The gel structure provides advantageous behavior of the coating both on a static and a dynamic point of view.

Indeed, the viscous part of the coating is linked to the gliding properties, while the elastic part is involved in getting a low activation force.

In particular, the gel structure avoids squeeze-out of the lubricant coating when a stopper is assembled within the barrel, with in turn reduces the activation force required to initiate movement of the stopper within the barrel; in addition, because of the visco-elastic properties of this gel structure, a low gliding force of the stopper is obtained when it is moved along the barrel.

Furthermore, the gel structure also provides a better resistance to the coating when submitted to autoclave.

This is particularly important because the coated container has to be subjected to at least one autoclave cycle (typically, in a saturated steam atmosphere at 120° C. under a pressure of 3 bars and during 20 minutes) in view of its sterilization.

As shown in the comparative examples below, the addition of a small fraction of acrylate-based silicone to a mixture of non-reactive silicone (such as PDMS) and vinyl-based silicone provides the gel structure after the irradiation step and the corresponding enhanced properties of the lubricant coating.

Indeed, a lubricant composition containing only non-reactive silicone (such as PDMS) and vinyl-based silicone does not lead to a gel structure after Co-60 irradiation.

Because of this missing tridimensional network, this lubricant coating is liquid and is not able to resist to an autoclave cycle.

The medical container on which such a coating can be applied may comprise a plastic or a glass barrel.

Plastic barrels are generally made of polyolefins such as high-density polyethylene, polypropylene, or cyclic polyolefins, or Crystal Clear Polymer.

The stopper may also be covered by a similar coating, at least on the surface that is in contact with the barrel.

However, if the barrel is coated, it may not be necessary to apply the lubricant coating to the stopper.

Once the lubricant composition has been applied on the barrel surface, it is submitted to irradiation such as Gamma-rays irradiation in order to cross-link the lubricant and to sterilize the barrel.

The barrel can then be filled with a liquid such as a liquid pharmaceutical composition, before being closed with a stopper to form the medical container.

Additionally, a further sterilization step, such as UV-rays or autoclave treatment can be performed before or after filling and closure of the medical container.

In an alternative embodiment, the barrel and the stopper can be lubricated in a first step before being assembled. The medical container is then submitted to irradiation such as Gamma-rays to achieve sterilization and cross-linking of the coating. Thereafter the corresponding medical container is filled with a liquid, such as a liquid pharmaceutical composition.

The prefilled medical container, closed by its stopper can then be sterilized by autoclave treatment in a final step.

Gliding tests after two autoclave cycles have been carried out on a 50 ml coated syringe filled with 50 ml of deionized water, the plastic barrel being lubricated and the butyl rubber stopper being non-lubricated.

The activation and gliding forces have been measured at a speed of 100 mm/min to be respectively below 30 N and 15 N.

On a chemical point of view, care must be taken to avoid extractable components within the lubricant composition.

Extractable components correspond to the chemical components that may be extracted from the lubricant coating and can migrate to the liquid pharmaceutical composition contained in the medical container. Volatile, semi-volatile and non-volatile contents as well as inorganic silicone content have thus to be measured in this liquid pharmaceutical composition.

With the medical container comprising a lubricant coating as described above, the extractable components are below the qualification threshold, which is currently of 5 µg/day for acrylate-based extractables.

Such chemical properties are particularly important in the case of prefilled medical containers in order to ensure both patient's safety and chemical stability of the pharmaceutical composition, because such containers are stored over a long period of time (typically, 12 to 24 months) before being used to perform an injection to a patient.

In this respect, it has been observed that a lubricant composition containing only PDMS and acrylate-based silicone (with a weight ratio of about 25%) lead to a viscous liquid after Co-60 irradiation but also provided a high extractable content, which is not acceptable.

COMPARATIVE EXAMPLES

Tests have been carried out on lubricant coating obtained from compositions consisting of three different silicone mixtures with different percentages (by weight) of PDMS 12500 cSt, VDT-731 vinyl-based silicone and UMS-182 acrylate-based silicone, the F3 composition corresponding to an embodiment of the present invention.

| Composition | PDMS 12500 cSt (% by weight) | Vinyl-based silicone (% by weight) | Acrylate-based silicone (% by weight) |
|---|---|---|---|
| F1 | 75 | 25 | — |
| F2 | 75 | — | 25 |
| F3 | 87 | 10 | 3 |

Each composition has been prepared according to the protocol described below.

After mixing of the different elements, each composition is degassed during about 2 hours.

Each composition, within a range between 3.4 to 5.4 mg, is then deposited onto the inner wall of a 50 ml barrel of Crystal Clear Polymer syringes with a siliconization bench, before submission to Gamma-irradiation with a Co-60 source with a dose of 25 KGy±3 so as to form the lubricant coating.

The siliconization bench consists, in this case, in a mobile nozzle, working at an atomization and jar pressure of about 2 bars, but any other kind of deposition methods can be used.

The same mixture as the one used to lubricate the syringes was also poured into a beaker to form a bulk volume (hereinafter referred to as "bulk composition"), and submitted to the same Gamma irradiation.

Then, the coated barrels are filled with water and closed with stoppers before being submitted to one or two autoclave cycles, each autoclave cycle being carried out at a temperature of 120° C. and a pressure of 3 bars during 20 minutes.

The stoppers have not been lubricated but Gamma irradiated at a dose of 25 KGy±3.

Influence of the Lubricant Repartition on the Surface of the Barrel

The repartition of the thickness T of the coating applied to the inner wall of the barrel has been measured with a RapId Layer Explorer equipment, the calibration of the equipment being done on a barrel without any lubricant or coating.

Figure 2:
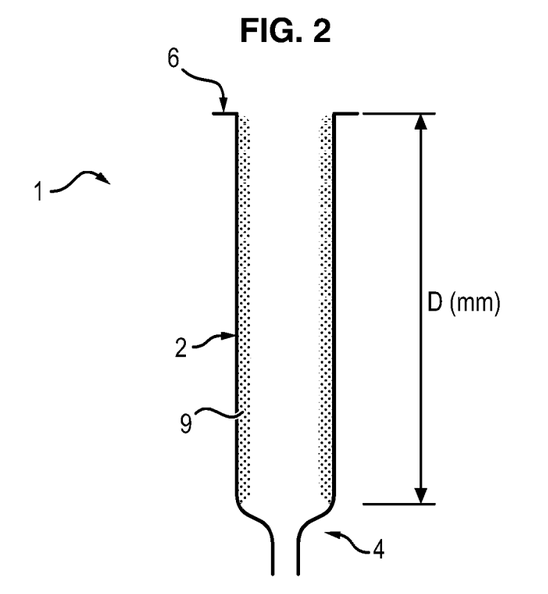
FIG. 2 show a syringe barrel coated with a lubricant coating according to the present invention.

The thickness of the coating 9 has been measured at different distances D from the flange 6 of the syringe 1 to the distal end 4 of the barrel 2 as shown on FIG. 2.

Figure 3:
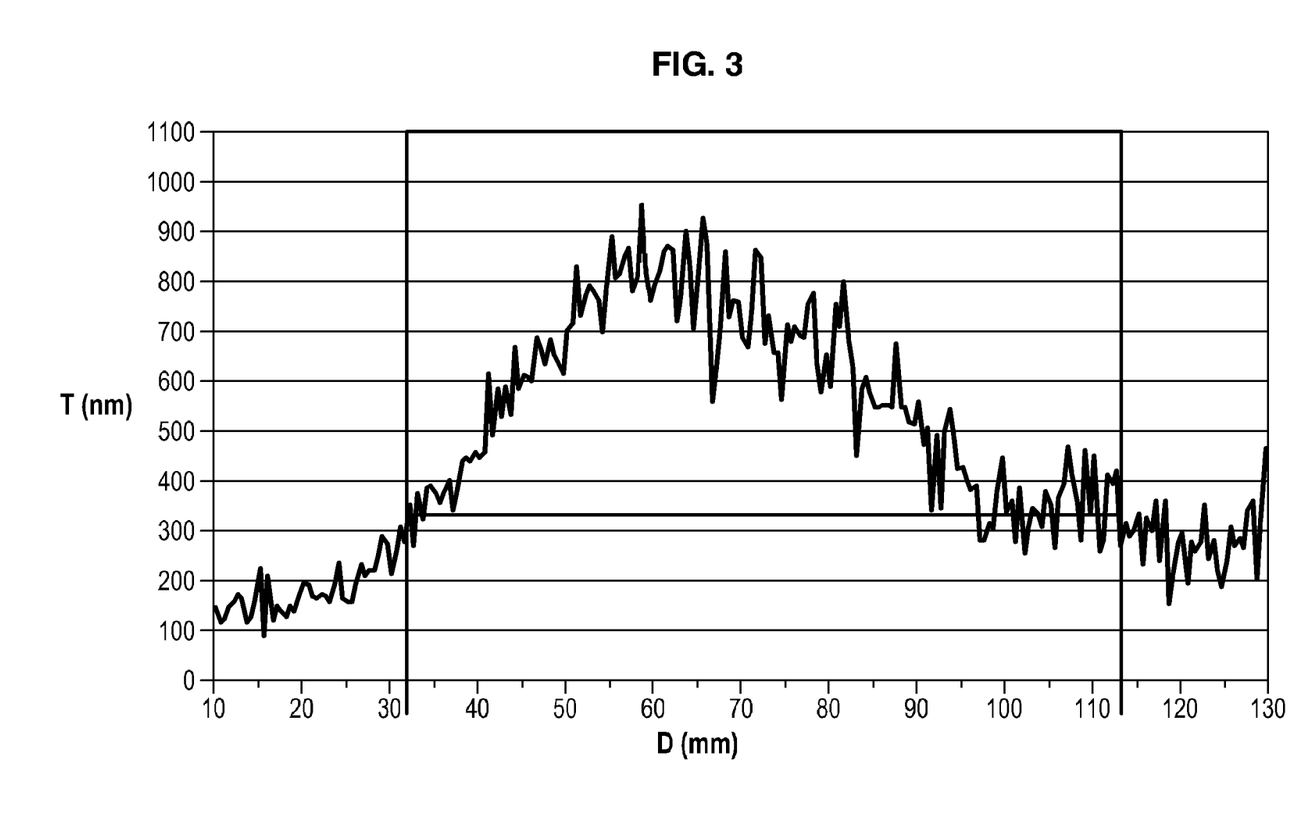
FIG. 3 shows the lubricant repartition on the inside surface of the barrel along the length of the barrel.

The curve shown on FIG. 3 presents the average thickness of the lubricant deposited on four 50 ml plastic barrels measured with the RapID.

As it can be seen on the FIG. 3, the repartition of the coating is not linear, and it has been decided to run the measurement of gliding and activation forces for thicknesses greater than 350 nm as this is the minimum thickness required to give good stopper activation.

Mechanical Tests

Some mechanical tests have been conducted to analyze the behavior of the stopper inside the barrel for the different coatings obtained from the F1, F2 and F3 compositions, i.e. coatings F1, F2 and F3.

The test consists in measuring the activation and gliding forces of the stopper after one autoclave cycle, the activation force being defined as the force required for putting in motion the stopper along the barrel, the gliding force being the force required for maintaining the movement of the stopper along the barrel.

To that end, a Lloyd LRX Plus bench has been used to induce the gliding of the stopper within the barrel and to measure the corresponding activation and gliding forces.

The activation force and the gliding force have been measured at a speed of 100 mm/min The measurements have been carried out for each coating F1, F2 and F3, each coating being applied on the barrel of two different 50 ml plastic syringes, the syringes being filled with 50 ml of deionized water.

The results are shown in the table below.

| Coating | Autoclave Cycle | Purge Activation Median Value (N) | Purge gliding Median Value (N) |
|---|---|---|---|
| F1 | 1 | 32.7 | 10.5 |
| F2 | 1 | 42.9 | 11.8 |
| F3 | 1 | 21.1 | 11.1 |

It can be seen from this table that the activation force is substantially lower with a coating according to the present invention (composition F3) than with the coatings obtained from the compositions F1 and F2.

This low value of activation force means that the stopper within a barrel lubricated with the F3 coating has a smooth initial gliding with a low stick-slip level allowing a more accurate dose delivering of the pharmaceutical composition to the patient.

Figure 4:
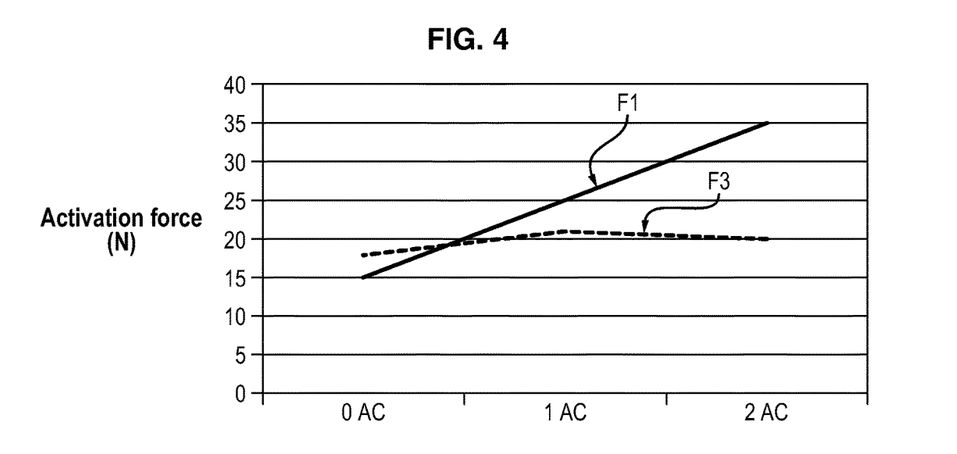
FIG. 4 shows the evolution of the activation force of the stopper with the number of autoclave cycles for different lubricant compositions.

FIG. 4 shows the evolution of the activation force according to the number of autoclave cycles submitted by the barrels coated with F1 and F3 coatings.

Indeed, the activation force for barrels coated with the F2 coating has not been evaluated as the activation force was already too high after one autoclave cycle.

It can be observed on FIG. 4 that whereas the activation force increases with the number of autoclave cycles for the F1 coating, which is detrimental to a smooth activation of the stopper, the activation force with the F3 coating is substantially stable over the autoclave cycles.

In other words, the autoclave cycles, which are required to sterilize the medical containers, do not damage the gliding properties of the coating according to the invention, which remains stable even after two autoclave cycles.

Moreover, the effect of ageing has been measured for the coating according to the invention. Such measurement has not been carried out for the F1 and F2 coatings as the ageing generally causes an increase of the activation force. Indeed, as the activation force was initially very high for these two compositions, it is obvious that the F1 and F2 coating would not give satisfactory results upon ageing.

Figure 5:
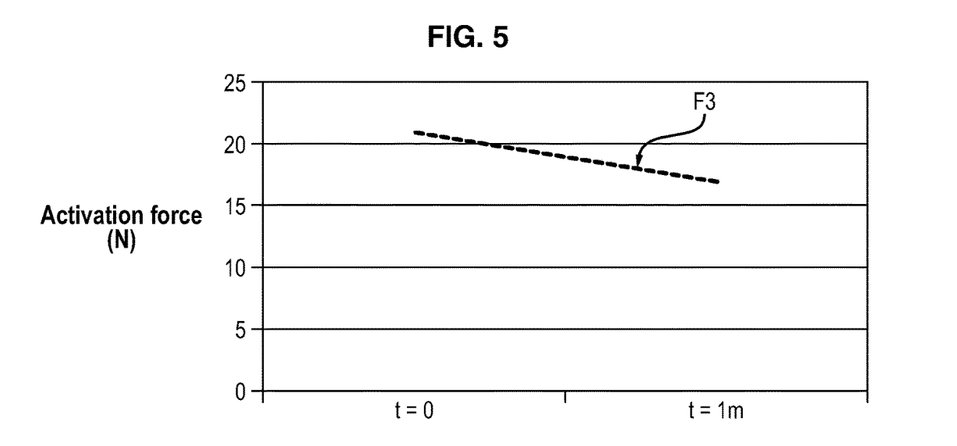
FIG. 5 shows the evolution of the activation force of the stopper over time for a composition according to the invention.

Therefore, FIG. 5 shows the evolution over time of the activation force of a syringe coated with the F3 coating, the first measurement being done at t=0 (i.e. after formation of the coating by application of the composition and irradiation) and the second measurement being done after one month.

It can be noted that ageing has the effect of slightly reducing the activation force, which is favorable to the initial gliding of the stopper.

The unique formulation of the F3 composition and especially the reactive silicone portion comprising both vinyl-based and acetate-based silicone therefore allows optimal gliding and activation forces, even after several autoclave cycles and/or extended storage time.

Gel Fraction

In another experiment, the gel percentage for the different coating F1, F2, F3 has been studied, after submission to Gamma irradiation. As the F1 coating does not have a gel structure after the Gamma irradiation, no data have been collected for this composition. The gel fraction is measured on the bulk composition, whose initial weight is measured.

During this test, a solvent (namely, toluene) is mixed with the coating during 12 hours, in order to swell the polymer and extract the free oil.

As the F2 coating is fully extracted with toluene, resulting in a substantially null gel fraction, the measurement of gel fraction by weight (or gel percentage) has been carried out only for the F3 coating.

Once the extraction done, the solution is filtered to collect the polymer, and the toluene is fully evaporated in an oven during 24 hours at 40° C.

The final weight of the dry polymer is then measured.

The gel fraction is the ratio between the final weight and the initial weight of the polymer.

For the F3 coating, the gel fraction is of about 35% by weight, as can be seen on the next table A significant gel fraction, meaning in a range comprised between 25 to 55%, is correlated to a good resistance to squeeze-out, in particular after autoclave treatment, as it indicates a dense tridimensional solid network formed by cross-linked vinyl-based and acrylate-based silicone enclosing the liquid non-reactive silicone.

As a result, the F3 coating with 35% of gel fraction can be considered as a product of choice for coating.

Visco-Elastic Properties

The visco-elastic properties (shear viscosity and phase angle) have been measured for each of the three F1, F2, F3 coatings when prepared as bulk compositions.

The shear viscosity (Pa·s) measures the resistance of a system to flow, meaning how much resistant is the system to an applied shear stress.

Therefore, the shear viscosity corresponds to the polymer resistance to deformation when sheared.

The phase angle (°) relies to the ability of the system to dissipate the mechanical energy into heat, knowing that the higher the phase angle is, the more dissipative the material is.

To that end, the bulk composition is loaded onto a rotational rheometer, with a gap between the lower plate and the upper plate of about 1 mm, the rheometer being rotated at frequencies between 100 and 0.1 rad/s, at 25° C.

The results with a shear rate of 0.1 rad/s are shown in the table below.

| Coating | Nominal Shear viscosity (Pa · s) | Phase angle (°) | Gel percentage (%) |
|---|---|---|---|
| F1 | N/A | N/A | 0 |
| F2 | 465 | 54 | 0 |
| F3 | 1200 | 35 | 35 |

As the F1 bulk coating does not have a gel structure, neither shear viscosity nor phase angle values have been measured for this composition.

Regarding the other bulk coating, the F2 coating has a high phase angle meaning that this is a highly dissipative material, with a low resistance to an applied shear stress due to its low share viscosity, and a high squeeze-out related to a null gel percentage.

On the contrary, the F3 coating has a higher resistance to an applied shear stress linked to its high value of shear viscosity, it is poorly dissipative as indicated by its low phase angle and it has a low squeeze-out correlated with a gel percentage of 35%. Therefore, these results confirm that the F3 coating has all the characteristics required to have a good gliding of a stopper inside a syringe barrel.

Indeed, it has been demonstrated that a coating with a shear viscosity comprised between 500 and 2000 Pa·s for a shear rate of 0.1 rad/s at 25° C., a phase angle comprised between 20° and 40° and a gel fraction comprised between 25 and 55% by weight would lead to very good coating properties.

Chemical Tests

Extractable components have been measured on the three coating F1, F2, F3 used as a coating for a syringe after ageing of one month at 40° C. in order to analyze the comportment of the coating with time.

In particular, several analyses have been performed to assess extractables from acrylate-based silicone in the syringes, such as volatile compounds with HS-GC/MS (acronym for Headspace-Gas Chromatography-Mass Spectrometry), semi-volatile compounds with Liq-GC/MS (acronym for Liquid Sample-Gas Chromatography-Mass Spectrometry), non-volatile detection with UPLC-DAD (acronym for Ultra High Performance Liquid Chromatography-Diode Array Detector), non-volatile identification with LC-Q-TOF (acronym for liquid Chromatography-Quadrupole Time-Of-Flight), acidic compounds with IC (acronym for Ionic Chromatography) and elemental analysis with ICP/MS (acronym for Inductively Coupled Plasma-Mass Spectrometry).

To run such experiments, once coated, 50 ml plastic syringes have been filled with water, closed with rubber stoppers and tip-caps. Then, the syringes have been autoclaved twice at 120° C. for 20 minutes, and stored for 1 month at 40° C.

sponds to an embodiment of the invention, the quantity is below the limit of detection (LOD), which is of around 100 ppb, or 5 μg.

Furthermore, it has to be noted that no extractable components has been found coming from the vinyl-based silicone present in the composition of the F1 and F3 coatings.

Therefore, the F3 coating is the product of choice for coating the inner wall of barrels as no by-product coming from acrylate or vinyl-based silicone would migrate into the pharmaceutical product contained into the syringes.

Mechanical Performance

In another experiment, the coating according to the present invention has been studied to analyze the mechanical performances of a syringe coated from such composition after autoclave treatment and ageing.

The table below summarizes the mechanical performances of a syringe coated with the F3 coating, wherein the 50 ml barrel has been sprayed with 4.4 mg of lubricant composition and Gamma irradiated with a dose of 25 kGy±3.

Each autoclave cycle is carried out at a temperature of 120° C. and a pressure of 3 bars for 20 minutes. Ageing is carried out by storage at 40° C. over one month.

The median value (med) and standard deviation (stdev) of activation and gliding forces are given in the table below.

|  |  | 0 autoclave cycle | | 1 autoclave cycle | | | 2 autoclave cycles | | | |
|---|---|---|---|---|---|---|---|---|---|---|
|  |  |  |  |  | Ageing | | | | | |
|  |  | T = 0 | | T = 0 | | T = 1 month | T = 0 | | T = 1 month | |
|  |  |  |  |  | Value | | | | | |
|  |  | med | stdev | med | stdev | med | stdev | med | stdev | med | stdev |
| Purge | Activation (N) | 17.6 | 1.9 | 21 | 3 | 17 | 1.1 | 20.1 | 2.1 | 23.3 | 3.3 |
|  | Gliding (N) | 7.4 | 0.8 | 11.1 | 1 | 8.8 | 0.7 | 10.4 | 1.4 | 8.8 | 0.6 |

In the table below are shown the concentrations and the quantities of an acrylate by-product determined by UPLC-DAD coupled with a MS/MS for the different coatings F1, F2 and F3. The quantification of this by-product is important to evaluate as it could migrate in the pharmaceutical solution or even interact with the pharmaceutical solution itself.

| Coating | By-product Concentration (ppb) | Average Acrylate by-product concentration (ppb) | Average Acrylate by-product quantity (μg/syringe) |
|---|---|---|---|
| F1 | N/A | N/A | N/A |
|  | N/A |  |  |
|  | N/A |  |  |
| F2 | 735 | 522 | 26 |
|  | 593 |  |  |
|  | 237 |  |  |
| F3 | <LOD | <LOD | <LOD |
|  | <LOD |  |  |
|  | <LOD |  |  |

As it can be seen in this table, no data have been generated for the F1 coating as its composition does not contain any acrylate-based silicone.

Nevertheless, the F2 coating produces a high amount of acrylate by-products with a level of 26 μg for a syringe, which is above the recommended threshold which is around 5 μg for a 50 ml syringe while the F3 coating that corre- As it can be seen from the table, the activation force increases slightly after one or two autoclave cycles, with or without ageing at 40° C.

It can then be concluded that the values of the activation forces remain in the same order of magnitude after autoclave and/or ageing.

Therefore, the F3 coating is very stable over time and after one or two autoclave cycles due to its tridimensional cross-linked network.

Concerning the gliding forces, the values are also slightly increasing.

Then it can be concluded that the autoclave treatment does not impact the gliding performance of the stopper along the wall of the barrel, meaning that the F3 coating remains stable over time despite autoclave treatments.

In conclusion, the combination of acrylate-based and vinyl-based silicone as a reactive silicone component in a lubricant composition comprising a mixture of reactive and non-reactive silicone promotes the provision, after irradiation, of a cross-linked lubricant coating that exhibits a gel structure conferring reduced activation and gliding forces (even after ageing and/or autoclave treatments), with null or limited extractable components.

While specific embodiments of the invention are described with reference to the figures, those skilled in the art may make modifications and alterations to such embodiments without departing from the scope and spirit of the invention. Accordingly, the above detailed description is intended to be illustrative rather than restrictive. The invention is defined by the appended claims, and all changes to the invention that fall within the meaning and range of equivalency of the claims are to be embraced within their scope.

The invention claimed is:

1. A medical container comprising a barrel having an inner surface and a stopper in gliding engagement with at least a portion of the inner surface of the barrel, wherein at least one of the barrel and the stopper are at least partially coated with a cross-linked lubricant composition comprising:
a mixture of non-reactive silicone with reactive silicone, wherein the reactive silicone comprises a mixture of vinyl-based silicone and acrylate-based silicone,
wherein the vinyl-based silicone is 10 weight % and the acrylate-based silicone is 3 weight % relative to the total weight of the lubricant composition.

2. The medical container of claim 1, wherein the lubricant composition has a coating thickness of at least 350 nm.

3. The medical container of claim 1, wherein the lubricant coating covers up to 90% of the inner surface of the barrel.

4. The medical container of claim 1, wherein the barrel is formed of plastic.

5. The medical container of claim 1, wherein the non-reactive silicone is between 80 and 90 weight % relative to the total weight of the lubricant composition.

6. The medical container of claim 1, wherein the non-reactive silicone is poly-(dimethylsiloxane).

7. The medical container of claim 1, wherein the vinyl-based silicone comprises a trimethylsilyl-terminated vinyl-methylsiloxane-dimethylsiloxane copolymer.

8. The medical container of claim 1, wherein the acrylate-based silicone comprises a trimethylsilyl-terminated acryloxypropylmethylsiloxane-dimethylsiloxane copolymer.

9. The medical container of claim 1, wherein the lubricant composition has a gel structure, the gel structure comprising a three-dimensional solid structure formed of cross-linked reactive functional groups of the reactive silicone and a liquid phase comprising non-reactive silicone, the liquid phase being retained within the three-dimensional solid structure.

10. The medical container of claim 1, wherein the lubricant composition has a gel structure comprising a gel fraction of between 25 and 55 weight %.

11. The medical container of claim 1, wherein the lubricant composition has a shear viscosity between 500 and 2,000 Pa·s for a shear rate of 0.1 rad/s at 25° C.

12. The medical container of claim 1, wherein the lubricant composition has a phase angle between 20° and 40° for a shear rate of 0.1 rad/s at 25° C.

* * * * *